(12) United States Patent
Mackles et al.

(10) Patent No.: US 7,192,573 B2
(45) Date of Patent: Mar. 20, 2007

(54) MOUTH RINSE WITH ENHANCED OXYGENATING ACTIVITY

(76) Inventors: Leonard Mackles, 311 E. 23rd St., New York, NY (US) 10010; William S Bess, 31 Greenwich Rd., Edison, NJ (US)

( * ) Notice: Subject to any disclaimer, the term of this patent is extended or adjusted under 35 U.S.C. 154(b) by 11 days.

(21) Appl. No.: 11/019,485

(22) Filed: Dec. 22, 2004

(65) Prior Publication Data

US 2006/0134021 A1 Jun. 22, 2006

(51) Int. Cl.
*A61K 8/00* (2006.01)
(52) U.S. Cl. .................. 424/53; 424/613; 424/49; 424/53; 424/56; 514/900
(58) Field of Classification Search .............. None
See application file for complete search history.

(56) References Cited

U.S. PATENT DOCUMENTS

| | | | | |
|---|---|---|---|---|
| 4,976,955 A | * | 12/1990 | Libin | 424/53 |
| 5,032,178 A | * | 7/1991 | Cornell | 106/35 |
| 6,348,187 B1 | * | 2/2002 | Pan et al. | 424/53 |
| 2004/0062798 A1 | * | 4/2004 | Lukenbach et al. | 424/465 |

* cited by examiner

*Primary Examiner*—Frederick Krass
*Assistant Examiner*—Lezah Roberts
(74) *Attorney, Agent, or Firm*—Omri M. Behr

(57) ABSTRACT

There are provided oral mouth rinse compositions, consisting essentially of: a) 1–20 wt % of an orally acceptable peroxide, b) 0.5–15 wt % of an orally acceptable sulfate, bisulfate, pyrosulfate salt of an inorganic cation or mixtures thereof, and c) water to 100 wt %. There are further provided methods of preparing and using said compositions as well as kits for maintaining the components to prepare said compositions.

30 Claims, No Drawings

MOUTH RINSE WITH ENHANCED OXYGENATING ACTIVITY

FIELD OF THE INVENTION

Anti bacterial and teeth whitening mouth rinse compositions.

BACKGROUND OF THE INVENTION

Oral mouth rinse compositions have been used for the prevention of bad breath, elimination of oral microorganisms that are responsible for bad breath, tooth decay, plaque, gum diseases such as gingivitis, and for whitening of the teeth. Oral mouth rinses containing hydrogen peroxide are well known for their ability to whiten teeth and reduce the bacterial flora in the oral cavity. Hydrogen peroxide is utilized due to its ability to decompose into water and oxygen, with the oxygen then acting as both an antimicrobial agent, and a bleaching agent to whiten teeth.

In the oral cavity, the decomposition of hydrogen peroxide into water and oxygen is aided by the enzyme peroxidase (also known as catalase). One factor affecting the rate of decomposition is the amount of peroxidase present in the oral cavity, with greater concentration resulting in greater decomposition. Thus, a mouth rinse that can cause an increase in the amount of peroxidase will have greater whitening and antimicrobial effectiveness.

Day U.S. Pat. No. 6,692,757 discloses a system for cleaning water lines, particularly in dental offices in which the peroxide decomposition is accelerated by the presence of an acidic sulfate. The presence of a disinfectant is also required. There is no disclosure or suggestion of oral use.

A second factor that will increase the rate of hydrogen peroxide decomposition is temperature. Higher temperature will increase the reaction rate between the peroxidase and peroxide, thus causing a faster onset of whitening and microbial kill. A heated mouth rinse will whiten teeth and kill microbes to a greater extent than an unheated mouth rinse of the same composition.

The generation of heat in solutions for hair bleaching and dying using a combination of hydrogen peroxide and sulfites is well known, but there has been no disclosure of suggestion of such combinations in the oral cavity.

SUMMARY OF THE INVENTION

The present invention provides a novel group of mouth rinses which enhance the activity of peroxide mouth rinses. This is achieved in two ways. The presence of orally acceptable inorganic cationic salts of sulfates, bisulfates or pyrosulfates in these rinses enhances the generation of saliva in the oral cavity and thus the level of peroxidase therein. This in turn causes a more rapid and efficient generation of active oxygen from the peroxide which in turn brings about greater whitening and microbial kill.

A particularly preferred embodiment utilizes an in-situ formation of sulfate, bisulfate pyrosulfate or mixture thereof from the reaction between sulfites, bisulfites or metabisulfites and peroxide to form sulfates. This embodiment suitably utilizes a 2-phase system that is mixed just prior to use in the oral cavity. Part 1 of the system contains an orally acceptable inorganic cation salt of sulfite, bisulfite, metabisulfite or mixture thereof. Part 2 contains an orally acceptable peroxide in an amount that exceeds the stoichiometric amount required to convert the sulfite, bisulfite, metabisulfite or mixture thereof, by at least 0.5%. Other ingredients such as flavor, ethanol etc. may optionally be included when desired, as described below.

During the reaction, not only is a sulfate and or a bisulfate formed but also the reaction is exothermic, which results in a temperature increase of about 3 to about 30 degrees centigrade depending on the concentrations employed. The resulting solution forms the mouth rinse, which if used substantially at once after formation, will provide not only increased salivary flow, but also increased temperature, both of which will increase the rate of peroxide decomposition, and result in greater antimicrobial efficacy and/or tooth whitening efficacy.

DESCRIPTION OF THE PREFERRED EMBODIMENTS

In order for the peroxidase acceleration of peroxide decomposition to be effective, the saliva stimulation must be effective but taste acceptable. Clearly this is an individual matter. While operative, concentrations above 10 wt % in the rinse have a salty taste, it is thus preferred to provide somewhat less salt, suitably between about 1.5 and about 6 wt % of the solution in the oral cavity.

For the reaction creating the oxidized salt to be sufficiently exothermic, sulfite, bisulfite or metabisulfite initial levels at the higher end of this range are preferred. Clearly there also needs to be not only the stoichiometric equivalent of peroxide to generate the exothermic reaction, but also sufficient excess peroxide to generate the active oxygen provided by the acceleration of decomposition caused by the rise in temperature. This excess should be at least 0.5 wt % of the solution used, but suitably may rise to about 5 wt %, though this should not be considered a limiting amount.

Thus the oral mouth rinse composition which is utilized suitably consists essentially of: a) 1–20 wt % of an orally acceptable peroxide, b) 0.5–15 wt % of an orally acceptable sulfate, bisulfate, or pyrosulfate salt of an inorganic cation or mixtures thereof, and c) water to 100 wt %. For example this may be prepared by mixing equal amounts of i) an aqueous solution consisting essentially of 2–40 wt % of the peroxide, and ii) an aqueous solution consisting essentially of 1–30 wt % of the said inorganic cation salt of a sulfite, bisulfite, metabisulfite or mixture thereof, provided that the amount of peroxide in (i) exceeds the stoichiometric amount required to completely oxidize the salt of the sulfite, bisulfite, metabisulfite or mixture thereof, by at least 1.0 wt %. Similarly, the final mouthrinse can be prepared by mixing unequal amounts of i) and ii) in such quantities as needed to achieve a final solution within the ranges specified above. Desirably, the components i) and ii) are contained in a kit of containers each containing one of these components.

Suitably, the peroxide is any orally acceptable peroxide, suitably hydrogen peroxide, urea peroxide or mixtures thereof and the cation is selected from the group consisting of sodium, potassium, ammonium, magnesium, calcium, aluminum, zinc, iron or mixture thereof.

The rinse may contain other ingredients conventionally used in mouth rinses. These include but are not limited to ethanol, flavor oils, sweeteners, and surfactant in an amount to enable solubilization of flavor oils, While in no way to be considered as limiting favorable ranges in the present invention provide peroxide/bisulfate mouth rinses consisting essentially of from about 1.5 to about 6 wt %, preferably about 3 wt % peroxide and from about 3 to about 10 wt %, preferably about 5 wt % bisulfate. Additionally the rinses may contain ethanol, flavor oils, sweeteners and surfactant in an amount to enable solubilization of flavor oils, and water.

EXAMPLES

Example 1

Pre-Brushing Mouth Rinse

| Ingredient | % by Weight |
|---|---|
| Ethanol | 5.00 |
| Flavor Oil | 0.10 |
| Benzoic Acid | 0.25 |
| Poloxamer 407(10% Aq. Sol'n) | 0.25 |
| Sucralose (1% Aq. Sol'n) | 15.00 |
| Water | 74.90 |
| Sodium Bisulfate | 3.00 |
| Disodium Pyrophosphate | 1.50 |
| Total | 100.00 |

Combine Ethanol, Flavor and Benzoic Acid. Mix until clear. While mixing, slowly add the Poloxamer, Sucralose, and water. Continue mixing and add the Sodium Bisulfate and Disodium Pyrophosphate. Mix until a clear solution is obtained.

Example 2

Breath Freshening Mouth Rinse

| Ingredient | % by Weight |
|---|---|
| Ethanol | 20.00 |
| Flavor Oil | 0.20 |
| Benzoic Acid | 0.25 |
| Magnesium Lauryl Sulfate | 0.20 |
| Sorbitol | 15.00 |
| Water | 61.85 |
| Sodium Bisulfate | 2.50 |
| Total | 100.00 |

Combine Ethanol, Flavor and Benzoic Acid. Mix until clear. While mixing, slowly add the Magnesium Lauryl Sulfate, Sorbitol, water and Sodium Bisulfate. Mix until a clear solution is obtained

Example 3

Two Phase Tooth Whitening Mouth Rinse

| Ingredient | % by Weight |
|---|---|
| Phase A: | |
| Ethanol | 10.00 |
| Flavor Oil | 0.20 |
| Magnesium Lauryl Sulfate | 0.27 |
| Sucralose (1% Aq. Sol'n) | 15.00 |
| Water | 61.53 |
| Sodium Bisulfate | 8.00 |
| Tromethamine | 5.00 |
| Phase A Total | 100.00 |
| Phase B: | |
| Hydrogen Peroxide(50% Aq. Sol'n) | 6.00 |
| Water | 94.00 |
| Phase B Total | 100.00 |

Phase A: Combine Ethanol, Flavor Oil and Magnesium Lauryl Sulfate. Mix until clear. While mixing, add the Sucralose, Water, Sodium Bisulfate, and Tromethamine. Mix until a clear solution is obtained.
Phase B: Combine the Hydrogen Peroxide and water. Mix until uniform Combine equal amounts of Phase A and Phase B, just prior to use, to form the final mouthrinse

Example 4

Two Phase Whitening Mouth Rinse (In-Situ Formation of Sodium Bisulfate)

| Ingredient | % by Weight |
|---|---|
| Phase A: | |
| Ethanol | 10.00 |
| Flavor Oil | 0.20 |
| Magnesium Lauryl Sulfate | 0.27 |
| Sucralose (1% Aq. Sol'n) | 15.00 |
| Water | 61.53 |
| Sodium Metabisulfite | 4.00 |
| Sodium Sulfite | 4.00 |
| Tromethamine | 5.00 |
| Phase A Total | 100.00 |
| Phase B: | |
| Hydrogen Peroxide(50% Aq. Sol'n) | 12.00 |
| Water | 88.00 |
| Phase B Total | 100.00 |

Phase A: Combine Ethanol Flavor Oil and Magnesium Lauryl Sulfate. Mix until clear. While mixing, add the Sucralose, water, Sodium Metabisulfite, Sodium Sulfite and Tromethamine. Mix until a clear solution is obtained.
Phase B: Combine the Hydrogen Peroxide and water. Mix until uniform Combine equal amounts of Phase A and Phase B, just prior to use, to form the final mouthrinse In accordance with the above formulation, but where in place of sulfite and/or the metabisulfite there is utilized only the metabisulfite, sulfite, or bisulfite, a similar solution is obtained.

In accordance with the above formulation, but where in place of sodium the cation utilized is potassium, ammonium, magnesium, calcium, aluminum, zinc, iron or mixture thereof a similar formulation is obtained.

Similarly in place of hydrogen peroxide, there may be utilized urea peroxide or mixtures thereof with hydrogen peroxide.

The formulation is utilized by introducing a comfortable amount, suitably about 10 ml, into the mouth agitating it, and ejecting it.

We claim:

1. An oral mouth rinse composition,
consisting essentially of:
a) 1–20 wt % of hydrogen peroxide
b) 0.5–15 wt % of an orally acceptable sulfate, bisulfate, pyrosulfate salt of an inorganic cation or mixtures thereof,
c) water to 100 wt % which is prepared by mixing
i) an aqueous solution consisting essentially of 2–40 wt % of the peroxide, and
ii) an aqueous solution consisting essentially of 1–30 wt % of the said inorganic cation salt of a sulfite, bisulfite, metabisulfite or mixture thereof, provided that the amount of peroxide in (i) exceeds the stoichiometric amount required to completely oxidize the salt of the sulfite, bisulfite, metabisulfite or mixture thereof by at least 1.0 wt % wherein all proportions are based on the weight of the final solution.

2. The composition of claim 1 wherein the final amount of salt is between about 1.5 and about 6.0 wt % wherein all proportions are based on the weight of the final solution.

3. The composition of claim 1 where the cation is selected from the group consisting of sodium, potassium, ammonium, magnesium, calcium, aluminum, zinc, iron or mixture thereof.

4. A method of preparing an oral mouth rinse composition,
consisting essentially of:
a) 1–20 wt % of an orally acceptable peroxide,
b) 0.5–15 wt % of an orally acceptable sulfate, bisulfate, pyrosulfate salt of an inorganic cation or mixtures thereof,
c) water to 100 wt %
which comprises mixing
i) an aqueous solution consisting essentially of 2–40 wt % of said orally acceptable peroxide and
ii) an aqueous solution consisting essentially of 1–30 wt % of said inorganic cation salt of a sulfite, bisulfile, metabisulfite or mixture thereof, provided that the amount of peroxide in (i) exceeds the stoichiometric amount required to completely oxidize the salt of the sulfite, bisulfite, metabisulfite or mixture thereof, by at least 1.0 wt % wherein all proportions are based on the weight of the final solution.

5. The method of claim 4 wherein the final amount of salt is between about 1.5 and about 6.0 wt % wherein all proportions are based on the weight of the final solution.

6. The method of claim 4 where the peroxide is hydrogen peroxide, urea peroxide or mixtures thereof.

7. The method of claim 5 where the peroxide is hydrogen peroxide, urea peroxide or mixtures thereof.

8. The method of claim 6 where the cation is selected from the group consisting of sodium, potassium, ammonium, magnesium, calcium, aluminum, zinc, iron or mixture thereof.

9. The method of claim 7 where the cation is selected from the group consisting of sodium, potassium, ammonium, magnesium, calcium, aluminum, zinc, iron or mixture thereof.

10. A method of enhancing the whitening and bactericidal activity of peroxide in the oral cavity comprising the steps of:
mixing aqueous solutions consisting essentially of
i) an aqueous solution consisting essentially of 2–40 wt % of an orally acceptable peroxide and
ii) an aqueous solution consisting essentially of 1–30 wt % of an inorganic cation salt of a sulfite, bisulfite, metabisulfite or mixture thereof, provided that the amount of peroxide in (i) exceeds the stoichiometric amount required to completely oxidize the salt of the sulfite, bisulfite, metabisulfite or mixture thereof, by at least 1.0 wt % wherein all proportions are based on the weight of the final solution and introducing said solution into the oral cavity.

11. The method of claim 10 wherein the mixture is introduced into the oral cavity promptly after its production.

12. The method of claim 10 wherein the final amount of salt is between about 1.5 and about 6.0 wt % wherein all proportions are based on the weight of the final solution.

13. The method of claim 10 where the peroxide is hydrogen peroxide, urea peroxide or mixtures thereof.

14. The method of claim 12 where the peroxide is hydrogen peroxide, urea peroxide or mixtures thereof.

15. The method of claim 13 where the cation is selected from the group consisting of sodium, potassium, ammonium, magnesium, calcium, aluminum, zinc, iron or mixture thereof.

16. The method of claim 14 where the cation is selected from the group consisting of sodium, potassium, ammonium, magnesium, calcium, aluminum, zinc, iron or mixture thereof.

17. A method of enhancing the whitening and bactericidal activity of peroxide in the oral cavity comprising introducing thereinto:
an queous solution consisting essentially of 1–20 wt % of hydrogen peroxide and of 0.5–15 wt % of an inorganic cation salt of a sulfate, bisulfate, pyrosulfate or mixture thereof wherein all proportions are based on the weight of the final solution.

18. The method of claim 17 wherein the mixture is introduced into the oral cavity promptly after its production.

19. The method of claim 17 wherein the amount of salt is between about 1.5 and about 6.0 wt % wherein all proportions are based on the weight of the final solution.

20. The method of claim 17 where the cation is selected from the group consisting of sodium, potassium, ammonium, magnesium, calcium, aluminum, zinc, iron or mixture thereof.

21. An oral mouth rinse composition,
consisting essentially of:
a) 1–20 wt % of hydrogen peroxide
b) 0.5–15 wt % of an orally acceptable sulfate, bisulfate, pyrosulfate salt of an inorganic cation or mixtures thereof,
c) water to 100 wt %
wherein all proportions are based on the weight of the final solution.

22. The composition method of claim 21 wherein the amount of salt is between about 1.5 and about 6.0 wt % wherein all proportions are based on the weight of the final solution.

23. The composition of claim 21, where the cation is selected from the group consisting of sodium, potassium, ammonium, magnesium, calcium, aluminum, zinc, iron or mixture thereof.

24. The composition of claim 22 where the cation is selected from the group consisting of sodium, potassium, ammonium, magnesium, calcium, aluminum, zinc, iron or mixture thereof.

25. A kit for preparing a warm mouthwash with enhanced oxidative action in the oral cavity consisting essentially of
i) a first container containing an aqueous solution consisting essentially of 2–40 wt % of an orally acceptable peroxide and
ii) a second container containing an aqueous solution consisting essentially of 1–30 % of an inorganic cation salt of a sulfite, bisulfite, metabisulfite or mixture thereof, provided that the amount of peroxide in (i) exceeds the stoichiometric amount required to completely oxidize the salt of the sulfite, bisulfite, metabisulfite or mixture thereof, by at least 1.0 wt % wherein all proportions are based on the weight of the final solution.

26. The kit of claim 25 wherein the final amount of salt is between about 1.5 and about 6.0 wt % wherein all proportions are based on the weight of the final solution.

27. The kit of claim 25 where the peroxide is hydrogen peroxide, urea peroxide or mixtures thereof.

28. The kit of claim 26 where the peroxide is hydrogen peroxide, urea peroxide or mixtures thereof.

29. The kit of claim 27 where the cation is selected from the group consisting of sodium, potassium, ammonium, magnesium, calcium, aluminum, zinc, iron or mixture thereof.

30. The kit of claim 28 where the cation is selected from the group consisting of sodium, potassium, ammonium, magnesium, calcium, aluminum, zinc, iron or mixture thereof.

* * * * *